United States Patent [19]

Wolff et al.

[11] Patent Number: 5,173,401

[45] Date of Patent: Dec. 22, 1992

[54] DETECTION OF NEISSERIA GONORROHOEAE

[75] Inventors: Karin Wolff, Germering; Anne Stern, Penzberg; Peter Buckel, Bernried; Erko Stackenbrandt, Danischenhagen, all of Fed. Rep. of Germany

[73] Assignee: Boehringer Mannheim GmbH, Mannheim, Fed. Rep. of Germany

[21] Appl. No.: 551,839

[22] Filed: Jul. 12, 1990

[30] Foreign Application Priority Data

Jul. 14, 1989 [DE] Fed. Rep. of Germany ....... 3923341

[51] Int. Cl.$^5$ ................ C12Q 1/68; G01N 33/566; C07H 15/12
[52] U.S. Cl. ..................... 435/6; 436/501; 536/26; 536/27; 536/28; 536/29; 935/77; 935/78
[58] Field of Search ............ 435/6, 29, 34, 320, 435/871; 536/26, 27, 28; 937/77, 78; 436/501, 94

[56] References Cited

FOREIGN PATENT DOCUMENTS 0237737 9/1987 European Pat. Off. ............ 536/27
8803957 6/1988 World Int. Prop. O. ............ 435/6

OTHER PUBLICATIONS

Rossau et al., Nuc. Acids Res. 16(13):6227 (Jul. 11, 1988).

Primary Examiner—Amelia Burgess Yarbrough
Assistant Examiner—Stephanie W. Zitomer
Attorney, Agent, or Firm—Nikaido, Marmelstein, Murray & Oram

[57] ABSTRACT

An oligonucleotide probe specific for *Neisseria gonorrhoeae* is selected from the oligonucleotides RS2* and RS3*, RS2 and RS3. It can have further nucleotides at its 5' end and/or 3' end. This probe is suitable for the specific detection of nucleic acids of the pathogenic species *N. gonorrhoeae* by hybrid formation under hybridization conditions.

4 Claims, No Drawings

DETECTION OF *NEISSERIA GONORROHOEAE*

BACKGROUND OF THE INVENTION

1. Field of the Invention

The invention concerns specific nucleic acid probes and a method for the detection of the pathogen *Neisseria gonorrhoeae*.

2. Description of the Prior Art

*N. gonorrhoeae* is the pathogen of gonorrhoea which is still today the most frequent notifiable infectious disease in the world (World Health Statistics Annual (1979), Geneva, WHO). In men, the genital infection manifests itself as a purulent inflammation and swelling of the urethra. These symptoms occur in 90% of cases of infection. If left untreated, the infection can ascend and after several weeks produce symptoms of prostatitis. In contrast, in women no or only slight symptoms occur in 50% of cases of infection. The infection primarily affects the cervix, but also the urethra. In 10 to 15% of women the infection spreads to the fallopian tubes which can also lead, inter alia, to sterility. In 1 to 3% of the cases a systemic invasion by the pathogen can occur in men and women which can lead to arthritis, endocarditis and peritonitis. Since the course of the infections is often asymptomatic, many carriers contribute unknowingly to the spread of the disease (Davis et al., In: Microbiology; Harper International Edition).

The species Neisseria is a group of closely related gram-negative diplococci which includes pathogenic as well as non-pathogenic species. The differentiation between *N. gonorrhoeae* and other non-pathogenic species which colonize the mucous membranes of man is therefore very important for the subsequent treatment. There is thus often the risk of mistake if the diagnosis of gonorrhoea is based solely on a microscopic examination.

A definitive diagnostic test for *Neisseria gonorrhoeae* requires the preparation of a culture. In this connection, difficulties often occur in the transport of material and the culture because the gonococci, as a result of their autolytic enzyme systems, are extremely sensitive to environmental influences such as change in temperature and dehydration. In addition, the culture is tedious since the incubation period is at least 20 hours. Furthermore, the culture as well as the definitive identification of the pathogen can be difficult and must therefore be carried out in special microbiological laboratories. The cultured gonococci are differentiated by carbohydrate degradation, oxidase reaction, antigen detection by coagglutination and fluorescent antibody screening.

A selective medium is used to culture *N. gonorrhoeae* on which, however, non-pathogenic Neisseria species such as e.g. *N. lactamica* can also grow. For this reason there is a risk of mistake which can only be excluded by exact and time-consuming biochemical differentiation. Attempts have therefore already been made to develop diagnostic tests which enable the rapid and specific detection of *Neisseria gonorrhoeae*.

In recent years, the technique of nucleic acid hybridization, which is attractive from the point of view of speed, has been developed for the identification of pathogenic organisms. Attempts have also been made to use nucleic acid probes for diagnosis with respect to *Neisseria gonorrhoeae*.

Nucleic acid probes have to fulfil two criteria in order to be used diagnostically. They must be specific i.e. the probe should only hybridize to the nucleic acid of the pathogen to be detected in order to exclude "false positive" test results. They must also be sensitive, i.e. the detection of only a few pathogens should also be possible in order to exclude "false negative" test results during an early stage of the infection.

A few years ago it was already recognized that it could be possible to specifically detect organisms using nucleic acid probes which are complementary to ribosomal RNA (rRNA). Such probes have the advantage that they are very sensitive since between 1000 copies and 10000 copies (of the rRNA) are present in each cell.

The method of identifying organisms using such rRNA-specific probes has already been described several times (EP-B 0155359, WO 84/02721, EP-A 0076123).

Also in the case of *Neisseria gonorrhoeae*, probes, whose sequences are complementary to regions of the 16S rRNA, have been used for the specific detection of this pathogen. In this connection, the sequence of the probes was derived from 3 regions of the 1544 nucleotide long 16S rRNA from *N. gonorrhoeae* (nucleotide position 125–150, 455–485, 980–1015). The above-mentioned probes were hybridized as a mixture to the entire RNA which was isolated from different Neisseria species (*N. gonorrhoeae*, *N. Meningitidis*, *N. cinerea*, *N. lactamica*, *N. mucosa* and *N. subflava*) and *Kingella kingae*. The probes were regarded to be specific for *N. gonorrhoeae* (EP-A 0272009).

This mixture of probes was tested with a selection of different species (see below). The investigation showed that the known probes hybridized with the nucleic acid of *Neisseria denitrificans*, a non-pathogenic species which is, however, closely related to *Neisseria gonorrhoeae*.

SUMMARY OF THE INVENTION

The object of the present invention was therefore, to provide detection probes for *Neisseria gonorrhoeae* which have an increased specificity compared to the rRNA probes known up to now and which thus enable a reliable qualitative and quantitative detection of pathogenic species.

DETAILED DESCRIPTION OF THE INVENTION

This object is achieved by a specific nucleotide probe for *Neisseria gonorrhoeae* which is selected from the oligonucleotide groups RS2 and RS3. An oligonucleotide of the group RS2 or RS3 is characterized in that its sequence or a part of its sequence is complementary to those regions R2 and R3 of the 16S rRNA of *Neisseria gonorrhoeae* which are shown in Table I.

TABLE 1

| Region | Nucleotide position on 16S rRNA of *N. gonorrhoeae* | |
|---|---|---|
| R2 | 820–860 | ATGTCAATTA GCTGTTGGGC AACTTGATTG CTTGGTAGCG T |
| R3 | 65–100 | GGACGGCAGC ACAGGGAAGC TTGCTTCTCG GGTGGC |

A specific detection of *Neisseria gonorrhoeae* is possible with these probes. Neither hybridization to closely related Neisseria species, such as *N. denitrificans* nor to other species is found. The high specificity of these probes is very important, since very many non-pathogenic Neisseria species, which are part of the human mucous membrane, can be present in one specimen (e.g. smear). Other organisms which colonize the human mucous membrane but which are not Neisseria species have therefore also been included in the screening for specificity.

Particularly good results in relation to the specificity are obtained with certain probes.

In a particularly preferred embodiment of the present invention the oligonucleotides RS2* or/and RS3* of 18 or 28 nucleotides length are used as the nucleic acid probes specific for *Neisseria gonorrhoeae* and whose sequence can be seen in Table II.

It is likewise particularly preferred to use nucleic acid probes for the detection of *N. gonorrhoeae* which are complementary to the complete region R2 or R3 and which are denoted RS2 or RS3 respectively. RS2 thus has a length of 41 nucleotides and RS3 is 36 nucleotides long.

The probes according to the present invention are at least 14 nucleotides long and can have further nucleotides, preferably up to 10 nucleotides, at thier 5' and/or 3' end.

In this case, the additional nucleotides of the probe can be any nucleotides; those nucleotides are, however, preferred which are complementary to the nucleotides which are present on the 16S rRNA at the 5' or 3' end.

The nucleic acid probes specific for *Neisseria gonorrhoeae* according to the present invention can furthermore be present in different forms. Thus, they can be present as single-stranded oligonucleotides, as double-stranded oligonucleotide fragments with a complementary oligonucleotide, or they can be associated with other sequences which have no homology to the DNA or RNA from *Neisseria gonorrhoeae* e.g. cloning vectors. Modified or unmodified ribonucleotides such as deoxyribonucleotides can also be used. In this case, it is also possible to subdivide into single-stranded vectors such as e.g. M13 and double-stranded vectors such as e.g. the pBR322 derivatives. Furthermore, the sequences of the detection probes can be coupled together in a single- or double-stranded form, so that two or more of these sequences are for example present in a vector. When using the double-stranded form the probe is separated into single-strands by denaturation before the actual detection reaction.

In a further preferred embodiment of the invention the nucleic acid probes are labelled. This is, in principle, possible via all the known methods of labelling; namely, the incorporation of radioactive isotopes or the incorporation of a non-radioactive label e.g. by incorporating modified nucleotides and a corresponding detection system.

A further object of the invention is a method for the detection of *N. gonorrhoeae* using at least one hybridizing probe under hybridization conditions and detection of the hybrid formation which is characterized in that one of the oligonucleotide probes according to the present invention is used for the specific detection.

The oligonucleotide probes according to the present invention hybridize to the rRNA as well as to the corresponding rRNA genes on the bacterial genome. Thus, in the method according to the present invention it is possible to determine the presence or absence of *N. gonorrhoeae* quantitatively and qualitatively by means of both types of nucleotides.

The detection by hybridization using at least one of the probes according to the present invention can be carried out using well-known methods for the detection of nucleic acids by hybridization. The DNA-DNA hybridization was described for the first time by Southern in J. Mol. Biol. 98 (1975) 503 and has subsequently been developed further. All suitable nucleic acid hybridization preparations can be used such as e.g. solid-phase hybridization, hybridization in solution, sandwich hybridization, two-component hybridization. The detection is then carried out either via a radioactive or non-radioactive labelling of the probe.

According to the present invention, it is possible by the use of the nucleic acid probe mentioned to carry out a rapid and reliable test for the presence of *N. gonorrhoeae* in a specimen and thus for an infection of the patient. The preparation of a culture is not necessary for this.

The following "Examples are non-limiting and disclose the preferred embodiments of the invention. Modifications which are obvious to those with skill in this art are subsumed by the disclosure and are presumed to be within the scope of applicants' invention.

EXAMPLE 1

The chromosomal DNAs of the following species were transferred onto a nitrocellulose filter using a slot-blot apparatus in which each DNA occupied one slot of the apparatus:

pathogenic Neisseria species:
*Neisseria gonorrhoeae*: 4 different isolates,
*Neisseria meningitidis*: 4 different isolates
non-pathogenic Neisseria species:
*N. lactamica*: 3 different isolates,
*N. mucosa*: 3 different isolates,
*N. subflava, N. perflava, N. sicca*: 2 different isolates,
*N. elongata, N. cinerea*: 2 different isolates,
*N. flava*: 2 different isolates,
*N. denitrificans*.

non-Neisseria species: *Haemophilus influenzae, Haemophilus parainfluenzae, Streptococcus salivarius, Streptococcus mutans, Streptococcus agalactiae, Staphylococcus aureus, Staphylococcus epidermidis, Staphylococcus saprophyticus, Escherichia coli, Kingella kingae.*

The preparation of the bacterial chromosomal DNAs was carried out according to the protocol described by Stern et al., Cell 37 (1984), page 447.

For this the filters were clamped into the apparatus, a vacuum was applied and the different application points were moistened with 200 μl 2× buffer (2× buffer: 2 mol/l NaCl, 50 mmol/l Tris-HCl, pH 7.5 and 1 mmol/l EDTA). 50 μl 50 mmol/l Tris-HCl, pH 7.5 and 5 mmol/l EDTA was added to the DNA and it was boiled for 3 min for the denaturation. Afterwards, the preparation was immediately transferred onto ice, 50 μl 2× buffer was added and this solution was pipetted into the slots. The slots were rinsed with 100 μl 1× buffer (2× buffer diluted 1:1 with water), the filter was taken out of the apparatus and dried in a vacuum. The hybridization was essentially carried out according to the described methods (Southern, J. Mol. Biol. 98 (1975), page 503).

In order to determine the species specificity, the synthesized oligonucleotides were hybridized to the chromosomal DNA from the different bacterial species bound to the filter. For this, the nitrocellulose filters were prehybridized for two hours in 1×PHB (2×PHB: 0.1% bovine serum albumin, 0.1% Ficoll 400000, 0.1% polyvinylpropylidone, 1% glycerol, 1.8 mol/l NaCl, 50 mmol/l Na₂HPO₄ and 10 mg/l herring sperm DNA). The herring sperm DNA contained in the PHB was previously denatured by heating to 80° C.

The hybridization was carried out in a hybridization oven at 42° C. The PHB was removed and substituted by the $^{32}$P-labelled oligonucleotide probe in hybridization buffer (HB) (HB: 1×PHB and addition of 0 to 30% formamide depending on the GC content of the probe). The HB was heated to 80° C. before use. After a hybridization time of at least 6 hours, the filters were at first washed twice at room temperature and subsequently they were washed twice at 42° C. in washing buffer (WB: 0.36 mol/l NaCl, 10 mmol/l Na₂HPO₄, 0.05% SDS). The washing temperature was increased to a maximum of 68° C. depending on the GC content of the sample. The actual maximum washing temperatures as well as the formamide content are also shown in Table II. In addition, this Table shows the sequences of the nucleic acid probes used, RS2* and RS3*.

TABLE II

| probe name | sequence of the probe 5'→3' | formamide content of the HB (%) | washing temperature (°C.) |
|---|---|---|---|
| RS2* | TACCAAGCAATCAAGTTG | 0 | 50 |
| RS3* | CCACCCGAGAAGCAAGCTTCCCTGTGCT | 30 | 68 |

The filters were exposed against an X-ray film.

The results of the hybridization of the different nucleic acid probes to pathogenic and non-pathogenic Neisseria species and non-Neisseria species is shown in Table III.

TABLE III

| Species[1]/Strain | Isolate No. | Oligonucleotide RS2* | RS3* |
|---|---|---|---|
| Neisseria gonorrhoeae | 74 | + | + |
| Neisseria gonorrhoeae | 514 | + | + |
| Neisseria gonorrhoeae | r2 | + | + |
| Neisseria gonorrhoeae | R16 | + | + |
| Neisseria meningitidis | B | − | − |
| Neisseria meningitidis | D | − | − |
| Neisseria meningitidis | 2-5 | − | − |
| Neisseria meningitidis | Z | − | − |
| Neisseria lactamica | 1855 | − | − |
| Neisseria lactamica | 2879 | − | − |
| Neisseria lactamica | 3272 | − | − |
| Neisseria mucosa | 112 | − | − |
| Neisseria mucosa | 114 | − | − |
| Neisseria mucosa | 2888 | − | − |
| Neisseria subflava | 124 | − | − |
| Neisseria perflava | 120 | − | − |
| Neisseria sicca | 2844 | − | − |
| Neisseria sicca | 118 | − | − |

TABLE III-continued

| Species[1]/Strain | Isolate No. | Oligonucleotide RS2* | RS3* |
|---|---|---|---|
| Neisseria elongata | 129 | − | − |
| Neisseria cinerea | 126 | − | − |
| Neisseria cinerea | 2199 | − | − |
| Neisseria flava | 122 | − | − |
| Neisseria flava | 123 | − | − |
| Neisseria denitrificans | 2950 | − | − |
| Haemophilus influenzae | 2214-1 | − | − |
| Haemophilus parainfluenzae | 1207 | − | − |
| Streptococcus salivarius | DSM 20067-1974 | − | − |
| Streptococcus mutans | ATCC 25175 | − | − |
| Streptococcus agalactiae | DSM 2104 | − | − |
| Staphylococcus aureus | 1472 | − | − |
| Staphylococcus epidermidis | ATCC 14990 | − | − |
| Staphylococcus saprophyticus | ATCC 15305 | − | − |
| Escherichia coli | 1424 | − | − |
| Kingella kingae | ATCC 23330 | − | − |

[1] classified according to Bergey's Manual of Systematic Bacteriology (1984) Krieg N. R., Holt J. G. (eds), Williams and Wilkins, Baltimore, pages 288 to 298.

We claim:

1. A *Neisseria gonorrhoeae*-specific oligonucleotide probe, selected from the group consisting of
   a) an oligonucleotide RS2* having the sequence TACCAAGCAA TCAAGTTG,
   b) an oligonucleotide RS3* having the sequence CCACCCGAGA AGCAAGCTTC CCTGTGCT,
   c) an oligonucleotide RS2** having the sequence ACGCTACCAA GCAATCAAGT TGCCCAACAG CTAATTGACA T and/or
   d) an oligonucleotide RS3** having the sequence GCCACCCGAG AAGCAAGCTT CCCTGTGCTG CCGTCC.

2. The probe according to claim 1, having up to 10 further nucleotides at its 5' and/or 3' end, said nucleotides corresponding to those nucleotides which are present at these positions in the natural gene from which the probes are derived.

3. The probe according to claim 1, having a detectable label.

4. A new method for the detection of the pathogenic Neisseria species *Neisseria gonorrheae* comprising:
   a) contacting under hybridizing conditions a sample suspected of containing *Neisseria gonorrheae* and an oligonucleotide probe according to claim 1; and
   b) detecting hybrid formation if *Neisseria gonorrheae* is present.

* * * * *